United States Patent
Howerzyl

(10) Patent No.: US 11,883,681 B2
(45) Date of Patent: Jan. 30, 2024

(54) BODY PART POSITIONING TABLE OR TABLE OVERLAY HAVING MULTIPLE MASK MOUNTING SYSTEMS

(71) Applicant: Medtec LLC, Orange City, IA (US)

(72) Inventor: Adam Howerzyl, Orange City, IA (US)

(73) Assignee: Medtec LLC, Orange City, IA (US)

( * ) Notice: Subject to any disclaimer, the term of this patent is extended or adjusted under 35 U.S.C. 154(b) by 659 days.

(21) Appl. No.: 17/012,585

(22) Filed: Sep. 4, 2020

(65) Prior Publication Data
US 2021/0069526 A1     Mar. 11, 2021

Related U.S. Application Data

(60) Provisional application No. 62/896,893, filed on Sep. 6, 2019.

(51) Int. Cl.
*A61N 5/10*       (2006.01)

(52) U.S. Cl.
CPC ........ *A61N 5/10* (2013.01); *A61N 2005/1097* (2013.01)

(58) Field of Classification Search
CPC .... A61N 5/00; A61N 5/10; A61N 2005/1097; A61B 2090/101; A61B 90/10; A61B 90/18
See application file for complete search history.

(56) References Cited

U.S. PATENT DOCUMENTS

| 5,473,784 | A | | 12/1995 | Nixon et al. |
| 5,531,229 | A | * | 7/1996 | Dean ...................... A61B 90/16 602/17 |
| 5,702,406 | A | * | 12/1997 | Vilsmeier .............. A61B 90/18 128/845 |
| 5,848,449 | A | * | 12/1998 | Hauger ................ A61B 6/0421 5/601 |

FOREIGN PATENT DOCUMENTS

| CN | 107812327 A | 3/2018 |
| CN | 108969900 A | 12/2018 |
| CN | 109453470 A | 3/2019 |
| EP | 2846694 A1 | 3/2015 |
| WO | 2017130296 A1 | 8/2017 |

\* cited by examiner

*Primary Examiner* — Fredrick C Conley
(74) *Attorney, Agent, or Firm* — Snyder, Clark, Lesch & Chung, LLP

(57) ABSTRACT

A body part positioning table or table overlay includes a planar surface to support a body part. The table or table overlay further includes a first mask mounting system having a first configuration for mounting a first mask that positions and secures the body part relative to the planar surface, and a second mask mounting system having a second configuration for mounting a second mask to position and secure the body part relative to the planar surface.

20 Claims, 12 Drawing Sheets

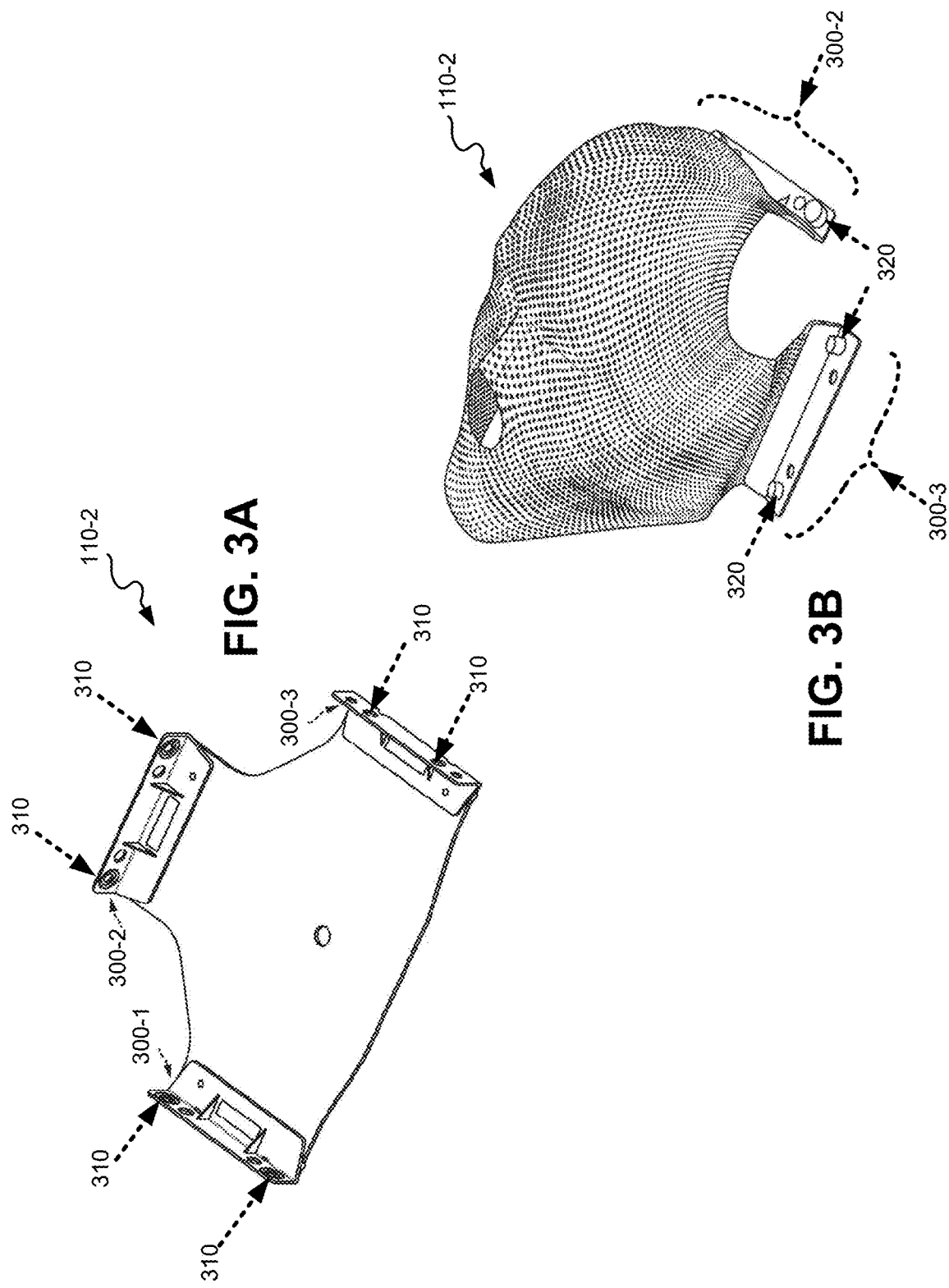

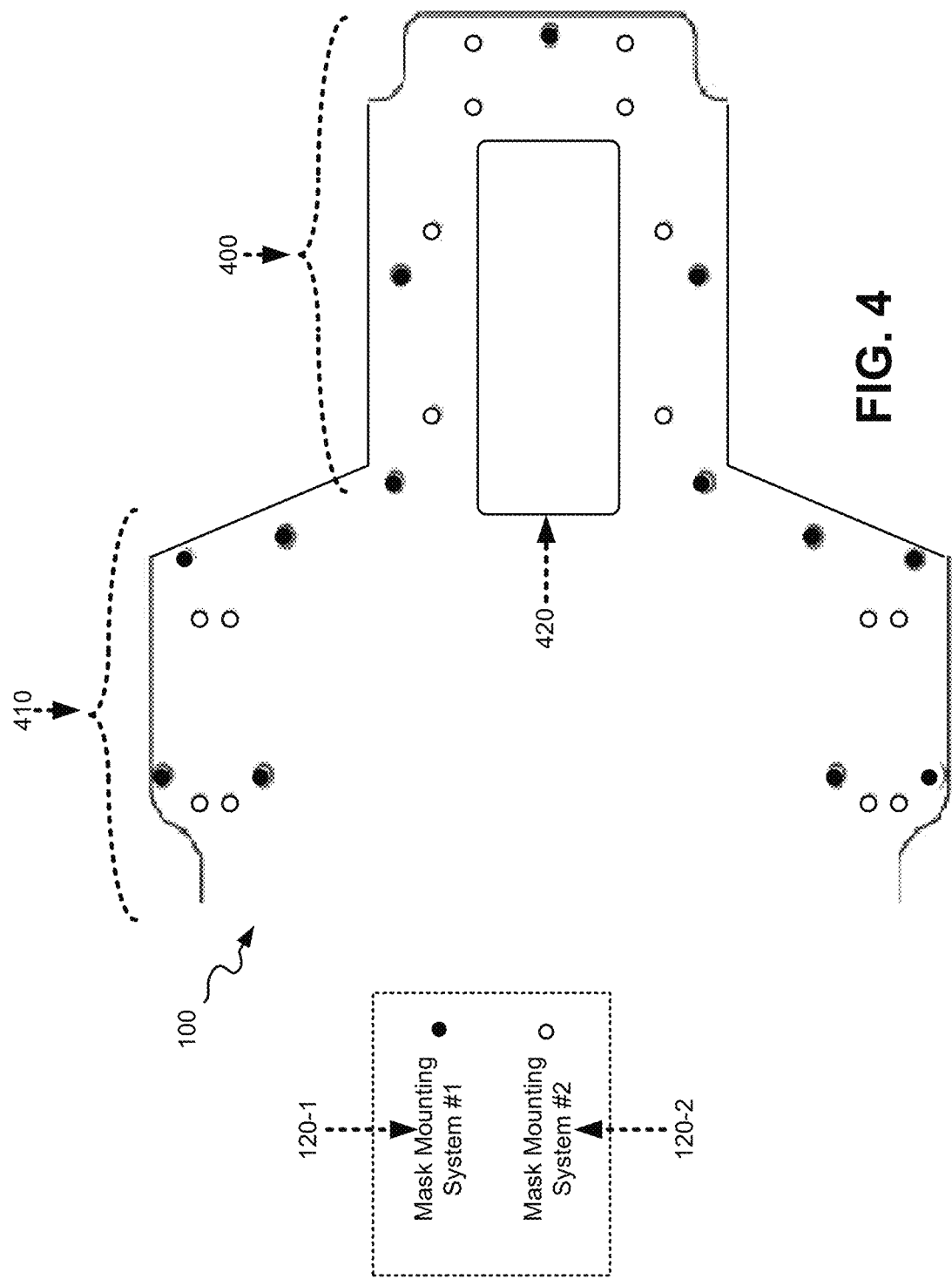

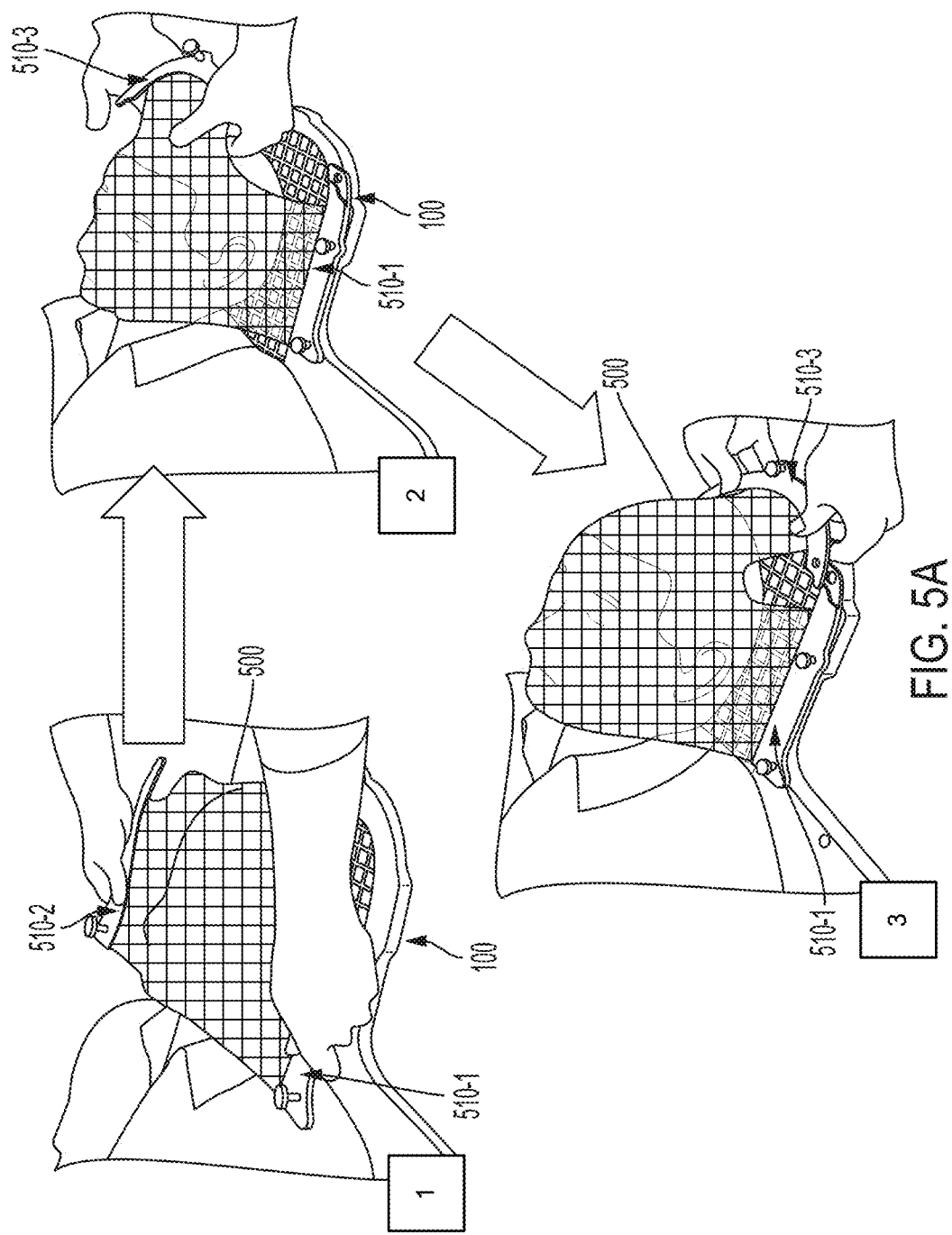

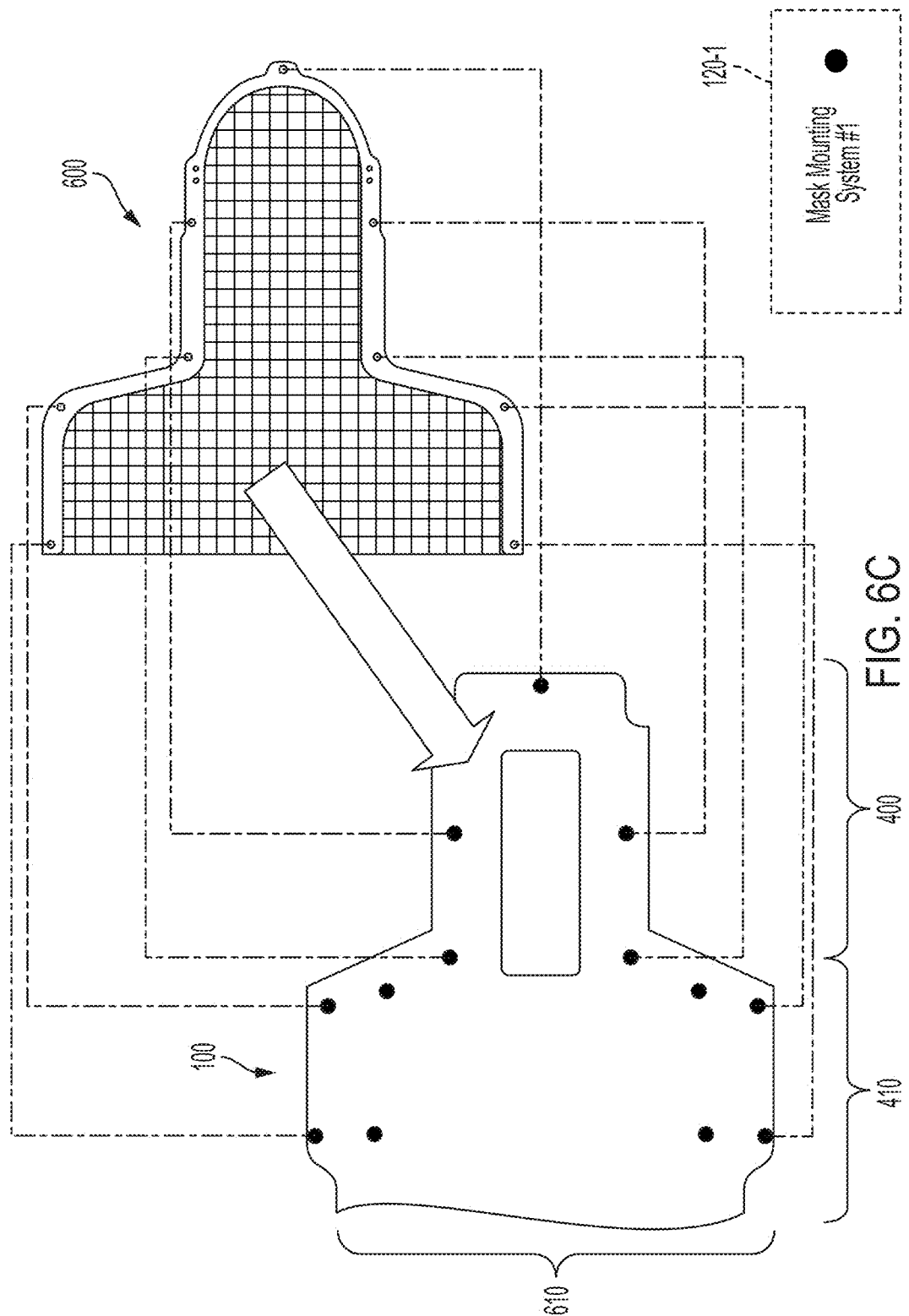

BODY PART POSITIONING TABLE OR TABLE OVERLAY HAVING MULTIPLE MASK MOUNTING SYSTEMS

CROSS-REFERENCE TO RELATED APPLICATION

This application claims priority under 35 U.S.C. § 119, based on U.S. Provisional Application No. 62/896,893, filed Sep. 6, 2019, the disclosure of which is hereby incorporated by reference herein.

BACKGROUND

Certain types of medical treatments or tests require that a portion of a human body be held in a same position to facilitate performance of the medical treatment or test upon that portion of the body. For example, when brain cancer patients undergo radiation treatment, their heads must be maintained in a precise, repeatable location for the treatment such that the underlying position of the brain tumor is fixed in space for the duration of the radiation treatment or treatments. Various different techniques have been used in the field of radiation oncology for holding body parts in a fixed position.

BRIEF DESCRIPTION OF THE DRAWINGS

FIGS. 3A and 3B illustrate details of a second mask of FIG. 1;

FIG. 4 depicts an exemplary implementation of the table/overlay of FIG. 1 that shows the physical arrangement of mask attachment structures associated with the multiple, different mask mounting systems;

FIGS. 5A and 5B depict a pictorial presentation of an example of mounting a mask to the table or table overlay, using one of the mask mounting systems of FIG. 1, to fix the position of a patient's head;

FIGS. 6A-6C depict the mounting of masks to the table or table overlay using a first mask mounting system.

DETAILED DESCRIPTION OF THE PREFERRED EMBODIMENTS

The following detailed description refers to the accompanying drawings. The same reference numbers in different drawings may identify the same or similar elements. The following detailed description does not limit the invention.

A technique, in the medical treatment/testing fields, for holding body parts in a fixed position uses heat-formable structures that include a sheet of retention material that is stretched over the body part of the patient. For example, for performing radiation treatment of a brain tumor, the heat-formable structure includes a mask having a sheet of retention material that is stretched over the patient's face. To form the mask over the patient's face, a hot water bath or oven may be first used to heat the material of the heat-formable structure such that the sheet of material becomes pliable and deformable. The heat-formable mask is then stretched over the patient's face, and the mask is allowed to cool and harden, permanently forming the mask to the shape of the face of the patient. As an example, a mask having a sheet of thermoplastic retention material, after heating, may be stretched over a patient's face, and then allowed to cool. Upon cooling, the mask, formed to the patient's face, creates a structure that can be used to hold the patient's head in a fixed position during radiation treatments. After the sheet of thermoplastic retention material of the mask is stretched over the body part of the patient, a frame portion of the mask is attached to a patient support table, a base, or other structure, using an attachment mechanism(s).

Exemplary embodiments described herein relate to a body part positioning table or table overlay that includes multiple mask mounting systems for mounting multiple different types of body part positioning masks. Body part positioning masks may have various different designs for various different purposes. Existing body part positioning tables or table overlays are designed with a single mask mounting system for mounting a single type of body part positioning mask. Therefore, existing body part positioning tables or table overlays are unable to accommodate different types of body part positioning masks that include attachment mechanisms that do not conform to the single mask mounting system. The table and table overlay(s) described herein employ multiple different mask mounting systems to enable the table and table overlay to accommodate multiple different types of body part positioning masks. The table and table overlays described herein may, thus, be designed as a "universal" body part positioning system that are capable of accommodating multiple different designs of body part positioning masks, with each different design of body part positioning mask having a unique configuration and type of attachment mechanisms.

Figure 1:
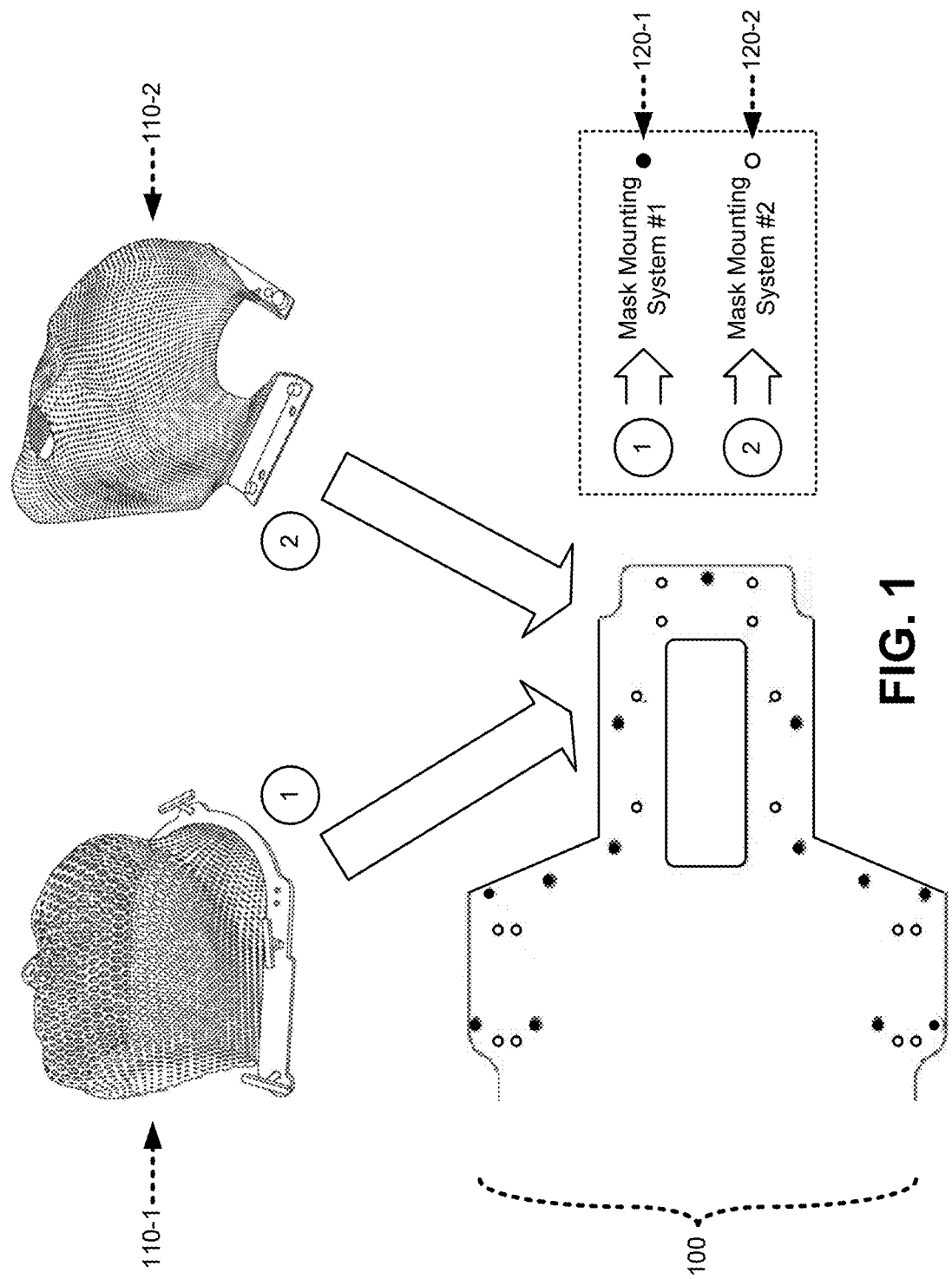
FIG. 1 illustrates an exemplary implementation of a table or table overlay that includes multiple mask mounting systems for mounting different masks to the table or table overlay.

FIG. 1 depicts an exemplary implementation of a table or table overlay 100 that includes multiple mask mounting systems for mounting different types of masks to the table or table overlay 100. In the exemplary implementation shown in FIG. 1, table or table overlay 100 (referred to herein as "table/overlay 100") includes two different mask mounting systems 120 for mounting two differently designed masks 110-1 and 110-2 (generically referred to herein as "mask 110" or "masks 110"). However, in other implementations, table/overlay 100 may include n different mask mounting systems for mounting n different types or designs of body part positioning masks, where n is greater than or equal to two. Table/overlay 100 includes a flat, planar member that, in one implementation, includes the table top of a treatment or testing table structure upon which a patient, a portion of the patient, a body part of the patient, or a portion of a body part of the patient, is placed. In another implementation, table/overlay 100 includes a planar member that may be placed over (i.e., on top of) an existing table-top of a treatment or testing table structure. Table/overlay 100 may have a flat upper surface with a size and shape to fit an entire patient or a portion of a patient, or to fit at least a body part or a portion of a body part of a patient. Table/overlay 110, therefore, may have various different shapes depending on the body part(s) of the patient being tested or treated. In some implementations, the upper surface of table/overlay 100 may not be entirely flat, but may, in certain locations, conform to one or more body parts of a patient. In other implementations, a body part rest structure (e.g., a head rest in the case of a patient's head) may be placed between the table/overlay 100 and the body part of the patient to provide a rest for the body part. In these implementations, the mask 110 may fit over both the body part and at least a portion of the underlying body part rest structure, when mounting the mask 110 to table/overlay 100, to secure the body part relative to the underlying table/overlay 100.

Masks 110 each includes any structure having a material (e.g., a thermoplastic material) that can be pulled over any body part(s) of a patient to form fit the material to the body part(s). In some embodiments, masks 110 enable the body part(s) to be immobilized and held in a specific position using fastening/attachment mechanism(s) that may, or may not, be a component of the masks 110 and which may operate as components of the mask mounting systems described herein. Masks 110-1 and 110-2 of FIG. 1 are shown as masks that are pulled over the head of a patient for positioning and holding the patient's head upon table/overlay 100. However, a "mask," as used herein, refers to any type of structure having a material that can be pulled over any body part(s) of a patient, or any portion of the body (that may include multiple body parts) of a patient, to form fit the material to the body part(s).

Mask 110 may include a mask frame that may be designed in a shape or shapes to fit over, or around, a specific body part(s) or portion of a body of a patient. The mask frame, as shown for mask 110-1 of FIG. 1, may include a single frame member. The mask frame, as shown for mask 110-2 of FIG. 1, may include a discontinuous frame composed of multiple separate frame members. Alternatively, the mask frame (not shown in FIG. 1) may include a discontinuous frame composed of multiple frame members that fit, connect, or snap together when attached to table/overlay 100 using the mask mounting system 120. The mask frame of mask 110 may be formed from various types of materials, including metal, plastic, carbon fiber, or a composite material. The mask frame of mask 110-1 is depicted as having a U-shape, where the sheet of form fitting material is attached within the inner region of the "U." Other shapes may, however, alternatively be used, such as, for example, a rectangular frame having one open side, a square frame having one open side, a triangular frame having one open side, etc.

The form fitting material may be attached to the mask frame of the mask 110 and may include various different types of form fitting materials. In one implementation, the form fitting material may include a sheet of thermoplastic material, such as a sheet of polycaprolactone (PCL), or a PCL/polyurethane blend. Other types of form fitting materials, including other types of polymers, may, however, be alternatively used. The sheet of form fitting material may include a sheet of material (e.g., thermoplastic) formed in a mesh pattern that includes a number of holes, openings, or perforations. The form fitting sheet of material may include materials that are stretchable (e.g., stretchable up to 400% from original dimensions in the case of a sheet of thermoplastic), and the sheet of form fitting material may be affixed to the mask frame using various techniques. For example, the sheet of form fitting material may be glued to the mask frame. As a further example, the sheet of form fitting material may be affixed to the mask frame using very high heat to melt the material such that it bonds with, or adheres to, the mask frame.

As shown in FIG. 1, table/overlay 100 includes multiple mask mounting systems (two mask mounting systems 120-1 and 120-2 shown by way of example) for mounting multiple different types of masks 110 to table/overlay 100. Each mask mounting system 120 may include multiple mask attachment structures located on, in, or through, the planar surface of table/overlay 100. In FIG. 1, the mask mounting structures for mask 110-1 are depicted as black circles having a first configuration on, in, or through table/table overlay 100, and the mask mounting structures for mask 110-2 are depicted as white or unfilled circles having a second configuration on, in, or through table/table overlay 100. The configuration of black circles includes a first physical arrangement of the mask attachment structures for mask 110-1 upon, in, or through the planar member of table/table overlay 100, and the configuration of white circles includes a second physical arrangement of the mask attachment structures for mask 110-2 upon, in, or through the planar member of table/table overlay 100, where the second physical arrangement is different than the first physical arrangement. The physical arrangement of the mask attachment structures for each mask mounting system 120 may be based on a shape and configuration of the mask frame of the mask 110 that is to be attached to table/overlay 100 using the mask mounting system 120. The mask attachment structures of each mask mounting system 120 may include different types of fastening/attachment mechanisms, including pins, screws, bolts, clamps, slots, retention holes, clips, anchors, straps, and/or latches. The fastening/attachment mechanisms of each mask mounting system 120 may be a component of, or integral to, table/overlay 100, and/or (as shown in FIG. 1) may be a component of, or integral to, mask 110.

Figure 2A:
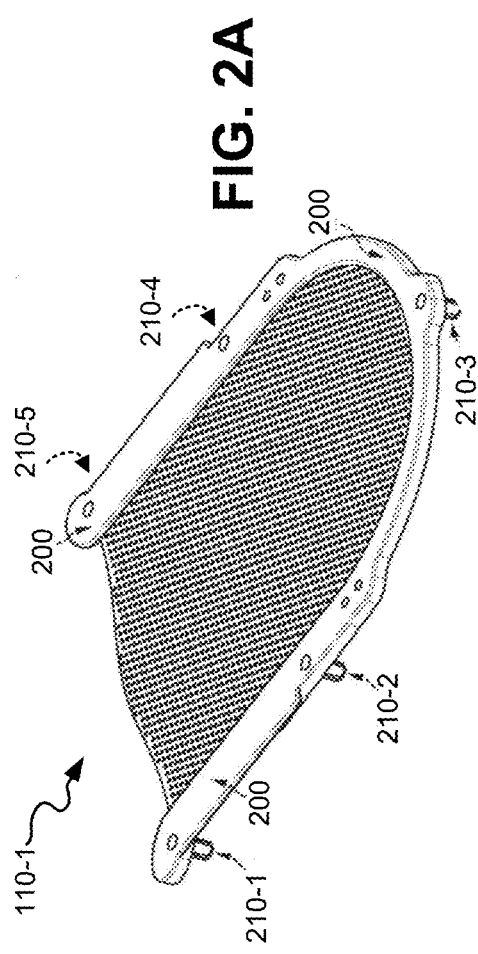
FIGS. 2A and 2B illustrate details of a first mask of FIG. 1.
Figure 2B:
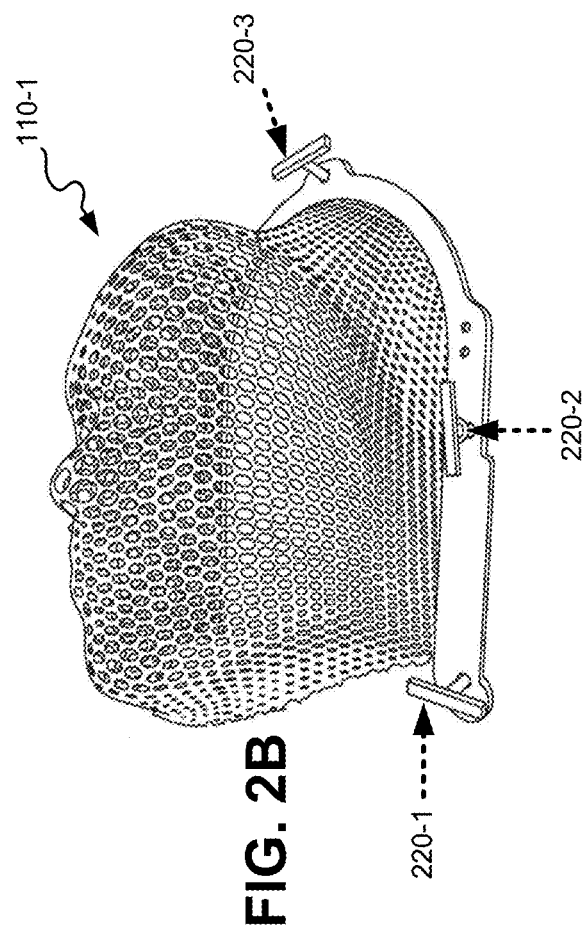

FIGS. 2A and 2B illustrate details of mask 110-1 of FIG. 1. As shown, a mask frame 200 of mask 110-1 includes a U-shaped frame having multiple alignment and retention holes (shown as 210-1, 210-2, 210-3, 210-4, and 210-5 in FIG. 2A) through which corresponding retention pins (pins 220-1, 220-2, and 220-3 shown in FIG. 2B; pins 220-4 and 220-5 not shown) may be inserted to fasten mask 110-1 to the underlying table/overlay 100 (not shown). In the implementation shown in FIG. 2A, retention holes 210 each includes a hollow, cylindrical pin that extends beneath the mask frame 200 to enable mask frame 200 to be aligned with corresponding retention holes in the underlying table/overlay 100 (not shown). Once the pins of retention holes 210 are inserted into the corresponding retention holes in the table/overlay 100, retention pins 220 may be inserted through each retention hole 210 into the corresponding retention holes in the table/overlay 100 to position mask frame 200 (and the body part(s) over which the form fitting material of mask 110 is stretched) in a fixed position relative to table/overlay 100.

FIGS. 3A and 3B illustrate details of mask 110-2 of FIG. 1. As shown, the mask frame of mask 110-2 includes a multi-piece frame that includes multiple frame members to which a sheet of form fitting material is connected within an inner region of mask 110-2 between the multiple frame members. In one embodiment, depicted in FIGS. 3A and 3B, mask 110-2 may include three frame members 300-1, 300-2, and 300-3, attached to the sheet of form fitting material around a perimeter of the sheet of form fitting material. For example, as shown, each of frame members 300-1, 300-2, and 300-3 may include an L-shaped frame member having a clip length that attaches to a different outer edge of the sheet of form fitting material. The sheet of form fitting material 120 has a length, on an open side of the sheet, and frame members 300-1, 300-2, and 300-3 are fastened to the sheet of material on each of the three other sides of the sheet. As shown, frame member 300-2 is fastened to an opposite side of the sheet of material (i.e., at a 12 o'clock position) from the open side having length $L_M$. Frame member 300-1 is fastened to a side of the sheet of material (i.e., at a 9 o'clock position) that is 90 degrees counterclockwise around the outside edge of sheet of material from frame member 300-2. Frame member 300-3 is fastened to a side of the sheet of material (i.e., at a 3 o'clock position) that is 90 degrees clockwise around the outside edge of the sheet of material from frame member 300-2.

As further shown in the embodiment of FIGS. 3A and 3B, each of frame members 300-1, 300-2, and 300-3 of mask 110-2 may include respective retention mounts 310 that permit mask attachment mechanisms 320 to be inserted into, and through, the retention mounts 310 such that the frame members 300-1, 300-2, and 300-3 of mask 110-2 can be mounted to table/overlay 100 to hold the patient's body part in a fixed position relative to table/overlay 100. Retention mechanisms 320, though shown in association with mask 110-2, may be components of mask mounting system 120-2. In the implementation shown in FIGS. 3A and 3B, retention mechanisms 320 each includes a pin that may be inserted through a retention mount 310 of frame members 300-1, 300-2, and 300-3 into corresponding retention holes, of mask mounting system 120-2 in the table/overlay 100, to position mask 110-2 (and the body part(s) over which the form fitting material of mask 110-2 is stretched) in a fixed position upon table/overlay 100. FIG. 3B depicts an example of mask 110-2 form fitted in the shape of a patient's face and head, with mask 110-2 attached to the underlying table/overlay 100 (not shown) using mask mounting system 120-2.

FIG. 4 depicts an exemplary implementation of table/overlay 100 that shows the physical arrangement of mask attachment structures associated with the multiple, different mask mounting systems 120. In the implementation shown in FIG. 4, the multiple, different mask mounting systems include mask mounting system 120-1 and mask mounting system 120-2. The arrangement of mask attachment structures of mask mounting system 120-1 are depicted with black circles upon table/overlay 100. The different arrangement of mask attachment structures of mask mounting system 120-2 are depicted as white or unfilled circles upon table/overlay 100. As shown, table/overlay 100 includes a head positioning region 400, and an upper body positioning region 410. Table/overlay 100 additionally may include an opening 420 within head positioning region 400 to enable the patient's face, when lying face down upon table/overlay 100, to extend below the upper surface of table/overlay 100. Head position region 400 includes a first set of mask attachment structures (e.g., black and white/unfilled circles), and upper body positioning region 410 includes a second set of mask attachment structures, of the mask mounting systems 120-1 and 120-2.

Figure 5B:
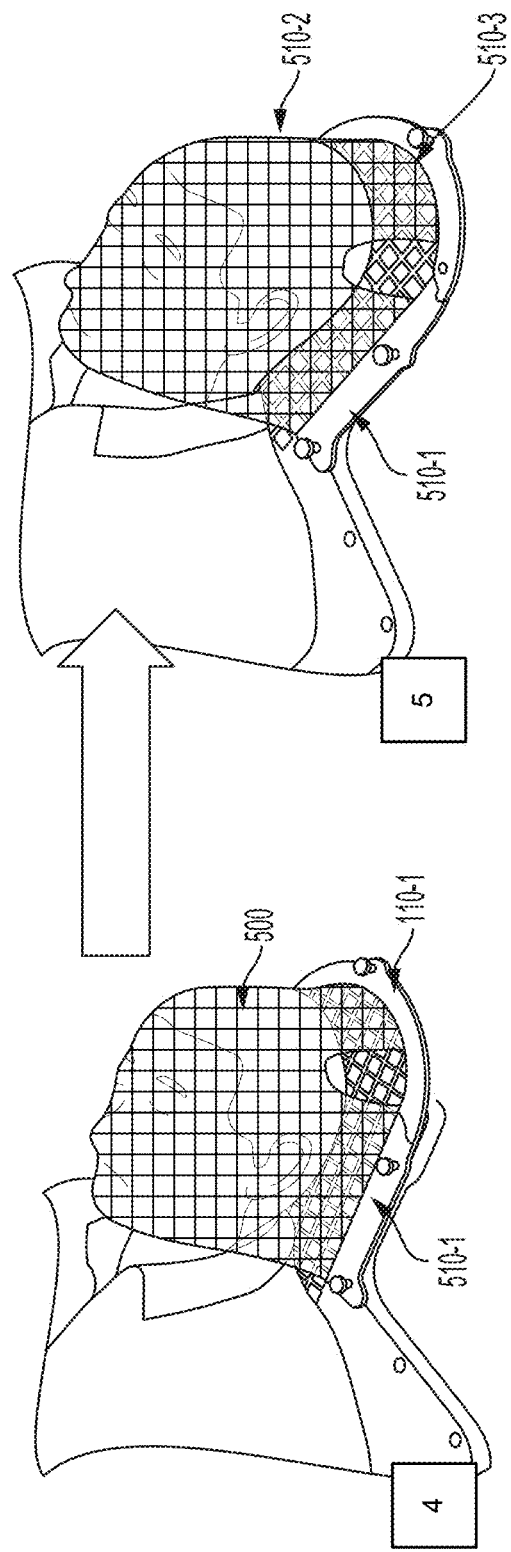

FIGS. 5A and 5B depict a pictorial presentation of an example of mounting a mask 110 to table/overlay 100, using mask mounting system 120-1 of FIG. 1, to fix the position of a patient's head. The temporal sequence of mounting mask 110 to table/overlay 100 is indicated in FIGS. 5A and 5B by sequential integers (i.e., each disposed within a square) associated with each image of the mask mounting process. In the example of FIGS. 5A and 5B, the mask frame of mask 110 includes three mask frame members that snap together when the three frame members are attached to table/overlay 100 using mask mounting system 120-1.

As shown at "1" in FIG. 5A, a sheet of form fitting material 500 of mask 110 is stretched over the face of the patient by holding onto mask frame members 510-1 and 510-2. As further shown at "2" in FIG. 5A, once frame members 510-1 and 510-2 are attached to table/overlay 100 using mask mounting system 120-1, frame member 510-3 may be pulled downwards to stretch the remaining portion of the sheet of form fitting material 500 of mask 110 in the vicinity of the forehead and top of the head of the patient. Frame member 510-3 is pulled downwards, as shown at "3" in FIG. 5A until the frame fastening mechanisms of frame member 510-3 mate with the fastening mechanisms of frame members 510-1 and 510-2 (shown at "4" in FIG. 5B). At "5" in FIG. 5B, mask 110 is shown with frame members 510-1, 510-2, and 510-3 fastened to base 100 using mask mounting system 120-1, and frame member 510-3 fastened to frame members 510-1 and 510-2 to create a single continuous mask frame. In the example of FIGS. 5A and 5B, the frame-to-table/overlay attaching mechanism of mask mounting system 120-1 includes retention pins that extend through mask 110 into table/overlay 100 in the particular physical arrangement (as shown in FIG. 1) of mask mounting system 120-1.

Figure 6A:
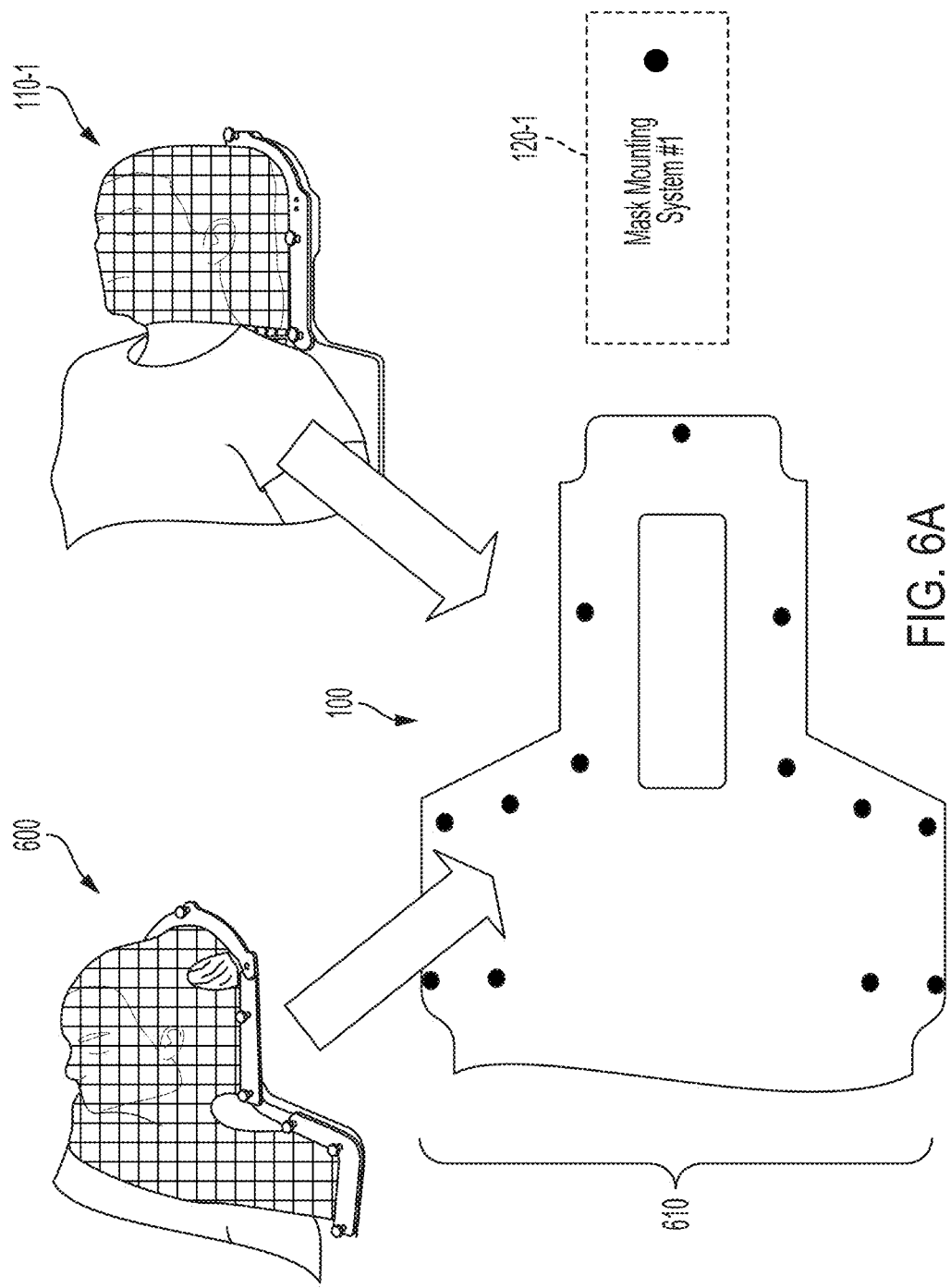
Figure 6B:
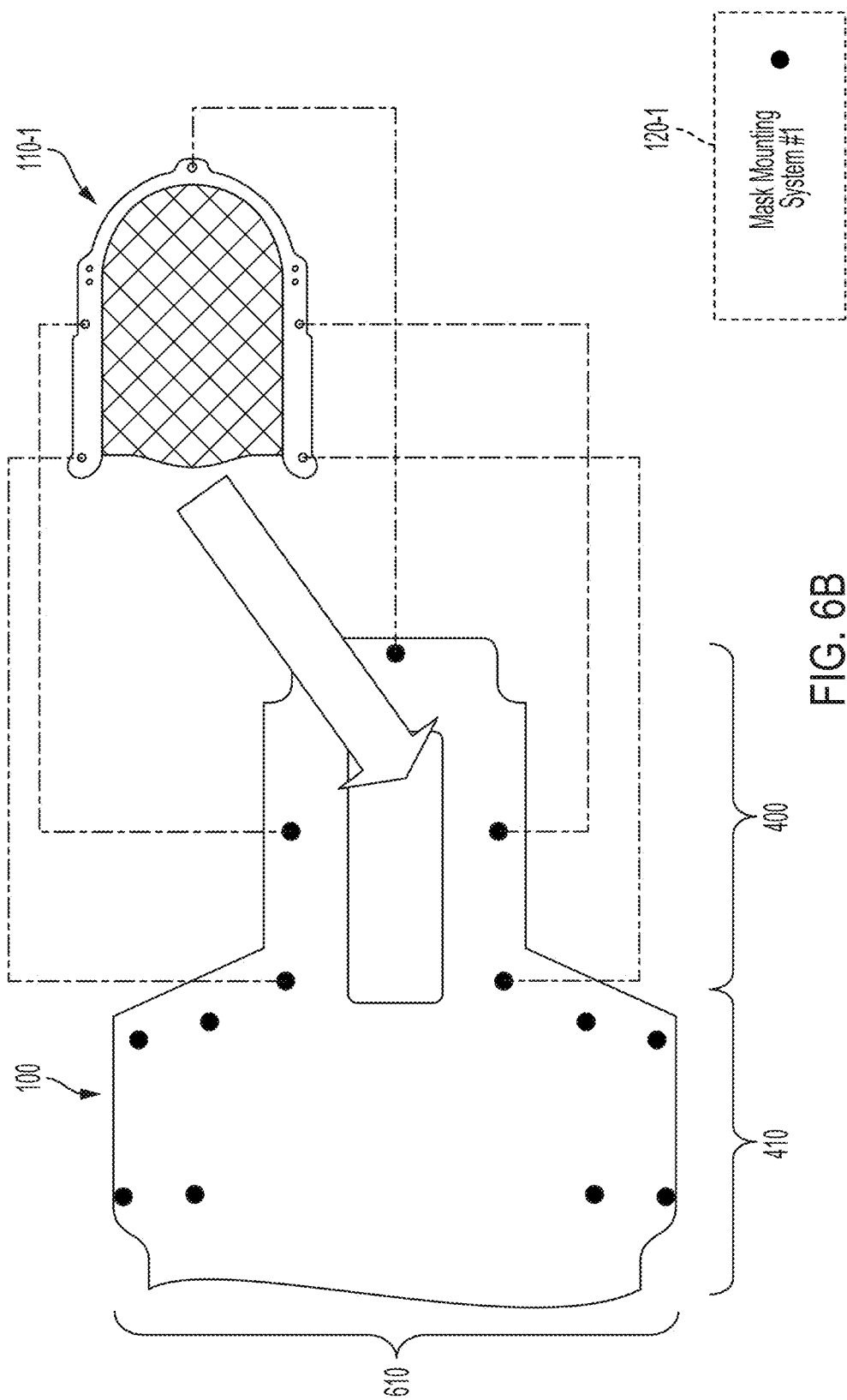

FIGS. 6A-6C depict the mounting of masks to table/overlay 100 using mask mounting system 120-1, including mask 110-1 that fixes a position of a head of a patient, and a mask 600 that fixes the position of the head and shoulders of the patient. For simplicity, FIGS. 6A-6C show only the mask attachment structures for mask mounting system 120-1, and not mask mounting system 120-2. As shown, table/overlay 100 includes a physical arrangement of mask attachment structures 610 upon, in, or through the upper surface of table/overlay 100 that is configured to accept corresponding attachment mechanisms on masks 110-1 and 600. In one implementation, the mask attachment structures of mask mounting system 120-1 include retention holes, and the corresponding attachment mechanisms of mask 110-1 and 600 include retention pins that extend through the mask frame member(s) of masks 110-1 and 600 into the underlying retention holes in table/overlay 100 to fix the position of the patient's head (i.e., mask 110-1) or the patient's head and shoulders (i.e., mask 600).

FIG. 6B illustrates the interconnections between the mask attachment structures 610 of table/overlay 100 and the corresponding attachment mechanisms of mask 110-1. Mask 110-1, which is intended to fix the position of the patient's head, attaches to the mask attachment structures 610 of mask mounting system 120-1 within the head positioning region 400 of table/overlay 100. FIG. 6C illustrates the interconnections between the mask attachment structures 610 of table/overlay 100 and the corresponding attachment mechanisms of mask 600. As shown, mask 600, which is intended to fix the position of the patient's head and shoulders, attaches to the mask attachment structures 610 of mask mounting system 120-1 within the head positioning region 400 and within the upper body positioning region 410 of table/overlay 100.

Figure 7A:
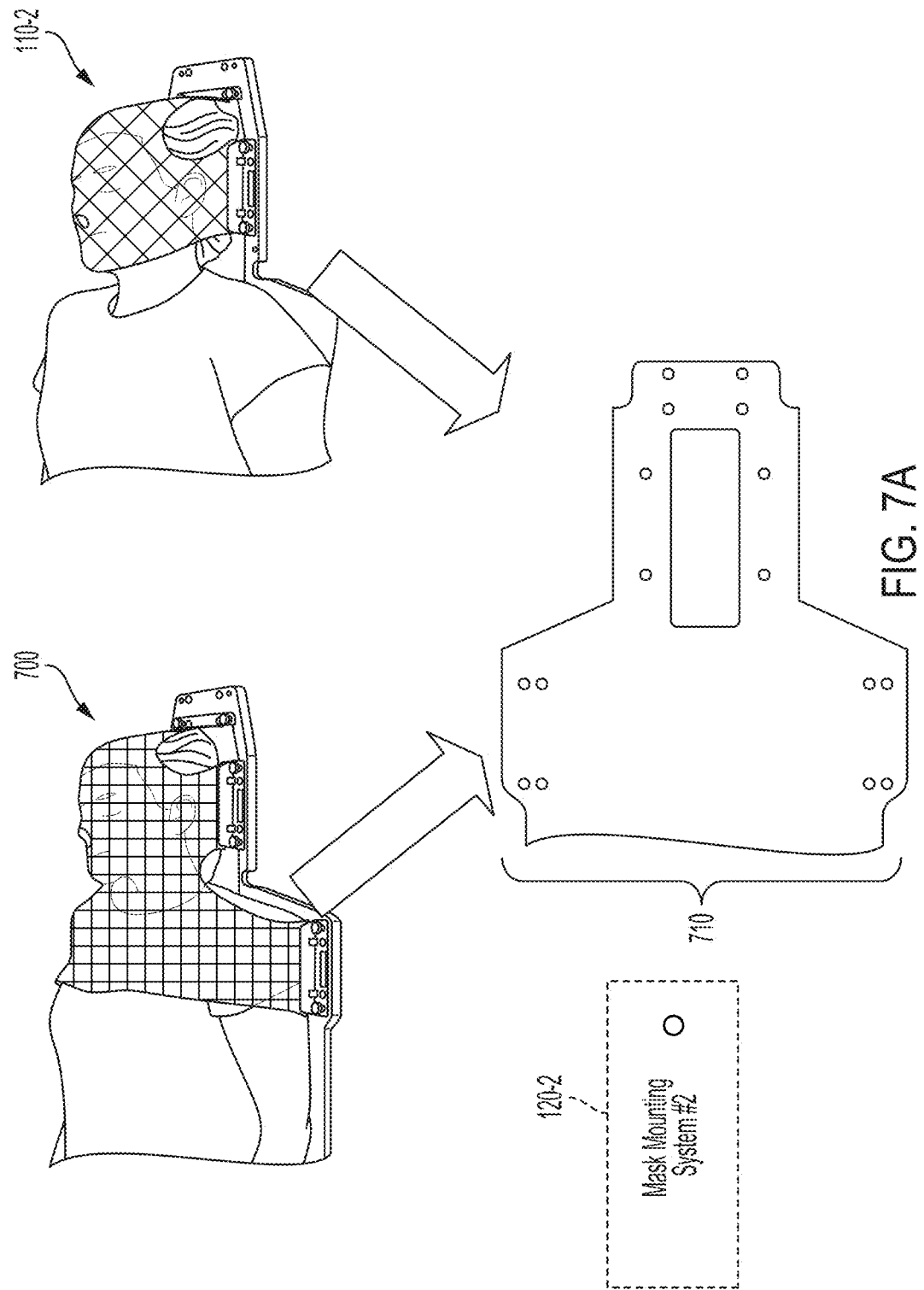
FIGS. 7A-7C depict the mounting of masks to the table or table overlay using a second mask mounting system that is different than the first mask mounting system of FIGS. 6A-6C.
Figure 7B:
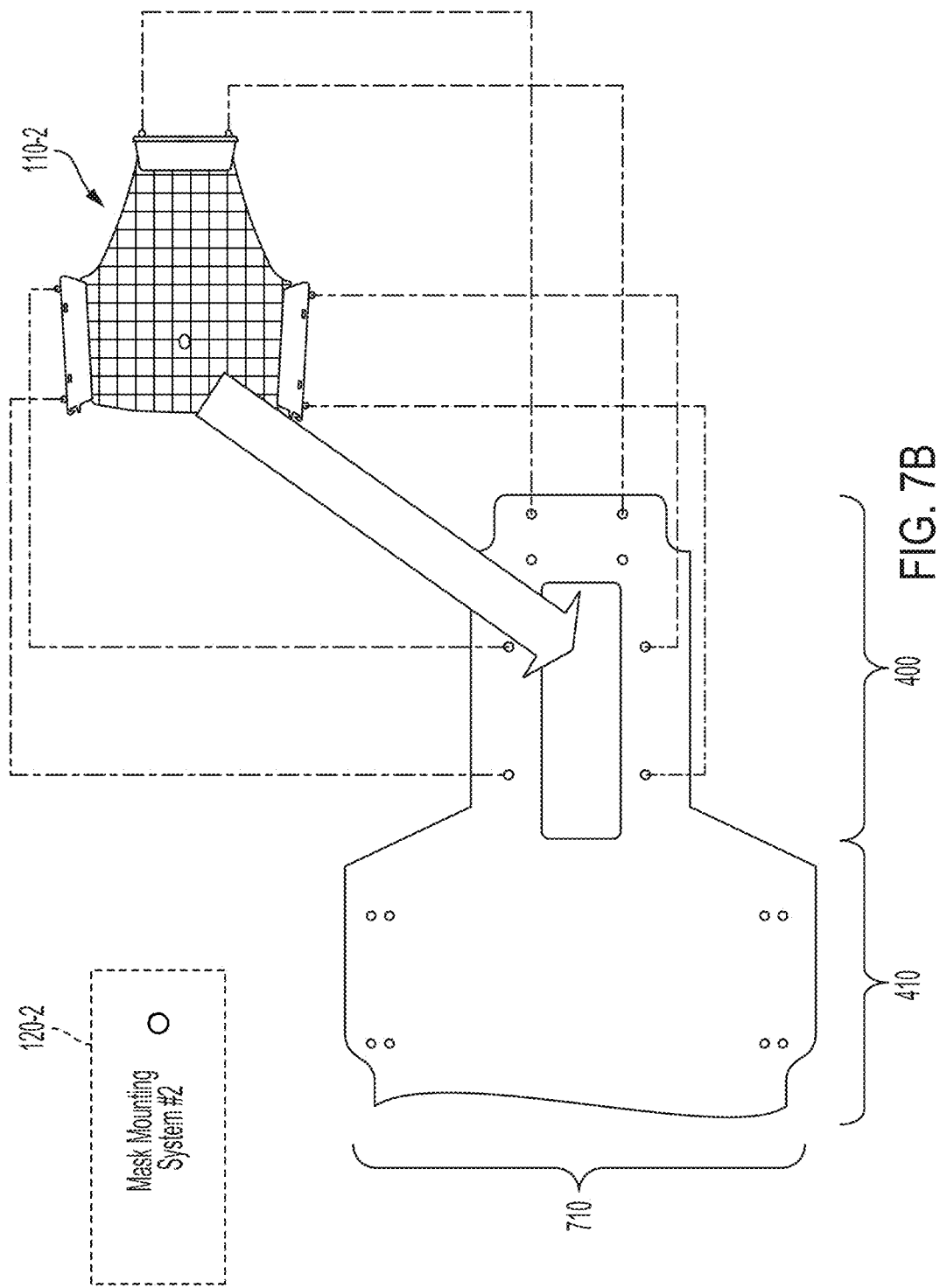
Figure 7C:
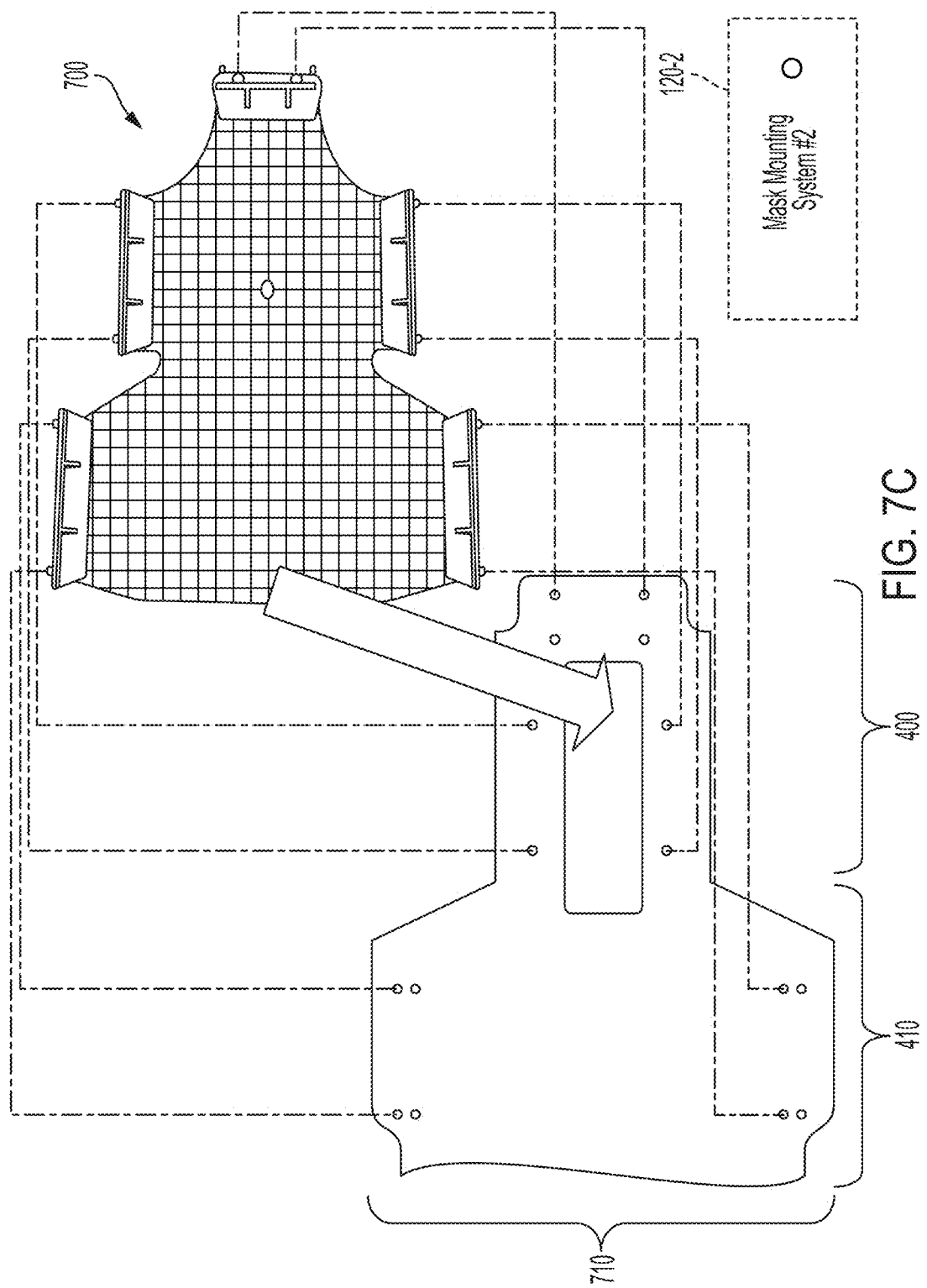

FIGS. 7A-7C depict the mounting of masks to table/overlay 100 using mask mounting system 120-2, including mask 110-2 that fixes a position of a head of a patient, and mask 700 that fixes the position of the head and shoulders of the patient. For simplicity, FIGS. 7A-7C show only the mask attachment structures for mask mounting system 120-2, and not mask mounting system 120-1. As shown, table/overlay 100 includes a physical arrangement of mask attachment structures 710 upon, in, or through the upper surface of table/overlay 100 that is configured to accept corresponding attachment mechanisms on masks 110-2 and 700. The physical arrangement of mask attachment structures 710 of the mask mounting system 120-2, shown in FIG. 7A, is different than the physical arrangement of mask attachment structures 610 of mask mounting system 120-1, shown in FIG. 6A. In one implementation, the mask attachment structures of mask mounting system 120-2 include retention holes, and the corresponding fastening/attachment mechanisms of masks 110-2 and 700 include retention pins that extend through the mask frame member(s) of masks 110-2 and 700 into the underlying retention holes in table/overlay 100 to fix the position of the patient's head (i.e., mask 110-2) or the patient's head and shoulders (i.e., mask 700).

FIG. 7B illustrates the interconnections between the mask attachment structures 710 of table/overlay 100 and the corresponding attachment mechanisms of mask 110-2. Mask 110-2, which is intended to fix the position of the patient's head, attaches to the mask attachment structures 710 of mask mounting system 120-2 within head positioning region 400 of table/overlay 100. FIG. 7C illustrates the interconnections between the mask attachment structures 710 of table/overlay 100 and the corresponding attachment mechanisms of mask 700. As shown, mask 700, which is intended to fix the position of the patient's head and shoulders, attaches to the mask attachment structures 710 of mask mounting system 120-2 within head positioning region 400 and upper body positioning region 410 of table/overlay 100.

The foregoing description of implementations provides illustration and description, but is not intended to be exhaustive or to limit the invention to the precise form disclosed. Modifications and variations are possible in light of the above teachings or may be acquired from practice of the invention.

Although the invention has been described in detail above, it is expressly understood that it will be apparent to persons skilled in the relevant art that the invention may be modified without departing from the spirit of the invention. Various changes of form, design, or arrangement may be made to the invention without departing from the spirit and scope of the invention. Therefore, the above-mentioned description is to be considered exemplary, rather than limiting, and the true scope of the invention is that defined in the following claims.

No element, act, or instruction used in the description of the present application should be construed as critical or essential to the invention unless explicitly described as such. Also, as used herein, the article "a" is intended to include one or more items. Further, the phrase "based on" is intended to mean "based, at least in part, on" unless explicitly stated otherwise.

What is claimed is:

1. A body part positioning structure, comprising:
   a planar member having an upper surface to support at least a portion of a body part, and further comprising:
   a first mask mounting system having a first physical arrangement of mask attachment structures, at first positions upon the upper surface, for mounting a first mask to secure the at least a portion of the body part upon the upper surface of the planar member; and
   a second mask mounting system having a second physical arrangement of mask attachment structures, at second positions upon the upper surface, for mounting a second mask to secure the at least a portion of the body part upon the upper surface of the planar member,
   wherein, when the first mask is mounted to the upper surface using the first mask mounting system, the second mask is precluded from also being mounted to the upper surface due to the first physical arrangement of the mask attachment structures, and
   wherein, when the second mask is mounted to the upper surface using the second mask mounting system, the first mask is precluded from also being mounted to the upper surface due to the second physical arrangement of the mask attachment structures.

2. The body part positioning structure of claim 1, further comprising:
   a third mask mounting system having a third physical arrangement of mask attachment structures, at third positions upon the upper surface, for mounting a third mask to secure the at least a portion of the body part upon the upper surface of the planar member.

3. The structure of claim 1, wherein the body part positioning structure comprises a table or table overlay.

4. The structure of claim 1, wherein the first mask comprises a first type of body part positioning mask and the second mask comprises a second, different type of body part positioning mask.

5. The structure of claim 1, wherein the first physical arrangement of mask attachment structures comprises an arrangement of the mask attachment structures in a first physical configuration upon the upper surface of the planar member, or in or through, the upper surface of the planar member, and
   wherein the second physical arrangement of mask attachment structures comprises an arrangement of the mask attachment structures in a second, different physical configuration upon the upper surface of the planar member, or in or through, the upper surface of the planar member.

6. The structure of claim 5, wherein the mask attachment structures comprise retention holes, wherein the first physical configuration comprises a first pattern of retention holes through the planar member, and wherein the second physical configuration comprises a second, different pattern of retention holes through the planar member.

7. The structure of claim 1, wherein each of the mask attachment structures comprises at least one of a pin, screw, bolt, clamp, retention hole, clip, anchor, strap, or latch.

8. A table or table overlay, comprising:
   a planar surface to support a body part, and further comprising:
   a first mask mounting system having a first configuration, encompassing a first area of the planar surface, for mounting a first mask that positions and secures the body part upon the planar surface; and
   a second mask mounting system having a second configuration, encompassing a second area of the planar surface, for mounting a second mask that positions and secures the body part upon the planar surface,
   wherein the first area and the second area overlap one another such that the first mask and the second mask cannot both be simultaneously mounted to the planar surface.

9. The table or table overlay of claim 8, wherein the first mask comprises a first type of mask and the second mask comprises a second, different type of mask.

10. The table or table overlay of claim 8, wherein the first mask mounting system comprises a first arrangement of mask attachment structures, and the second mask mounting system comprises a second arrangement of mask attachment structures.

11. The table or table overlay of claim 10, wherein the first arrangement of mask attachment structures comprises an arrangement of the mask attachment structures in a first physical configuration upon, in, or through the planar surface, and
   wherein the second arrangement of mask attachment structures comprises an arrangement of the mask attachment structures in a second, different physical configuration upon, in, or through the planar surface.

12. The table or table overlay of claim 10, wherein each of the mask attachment structures comprises at least one of a pin, screw, bolt, clamp, retention hole, clip, anchor, strap, or latch.

13. The table or table overlay of claim 11, wherein the mask attachment structures comprise retention holes, wherein the first physical configuration comprises a first pattern of retention holes through the planar surface, and wherein the second physical configuration comprises a second, different pattern of retention holes through the planar surface.

14. The table or table overlay of claim 8, further comprising:
a third mask mounting system having a third configuration, encompassing a third area of the planar surface, for mounting a third mask that positions and secures the body part upon the planar surface,
wherein the first area, the second area, and the third area overlap one another such that any two of the first mask, the second mask, or the third mask cannot be simultaneously mounted to the planar surface.

15. A body part positioning structure, comprising:
a planar member having an upper surface to support at least a portion of a body, and further comprising:
a first mask mounting system for mounting a first mask to position and secure the at least a portion of the body to the upper surface of the planar member; and
a second mask mounting system for mounting a second mask to position and secure the at least a portion of the body relative to the upper surface of the planar member,
wherein the first mask mounting system comprises a first physical arrangement of mask attachment structures on, in, or through the upper surface of the planar member, wherein the first physical arrangement of mask attachment structures encompasses a first area of the upper surface of the planar member,
wherein the second mask mounting system comprises a second physical arrangement of mask attachment structures on, in, or through the upper surface of the planar member, or in or through the upper surface of the planar member, wherein the second physical arrangement of mask attachment structures encompasses a second area of the upper surface of the planar member, and
wherein the first area overlaps the second area such that the first mask and the second mask cannot both be simultaneously mounted to the upper surface of the planar member.

16. The structure of claim 15, wherein the body part positioning structure comprises a table or table overlay.

17. The structure of claim 15, wherein each of the mask attachment structures comprises at least one of a pin, screw, bolt, clamp, retention hole, clip, anchor, strap, or latch.

18. The structure of claim 15, wherein the mask attachment structures comprise retention holes, wherein the first physical arrangement comprises a first pattern of retention holes through the planar member, and wherein the second physical arrangement comprises a second, different pattern of retention holes through the planar member.

19. The structure of claim 15, further comprising:
a third mask mounting system for mounting a third mask to position and secure the at least a portion of the body to the upper surface of the planar member,
wherein the third mask mounting system comprises a third physical arrangement of mask attachment structures on, in, or through the upper surface of the planar member,
wherein the third physical arrangement of mask attachment structures encompasses a third area of the upper surface of the planar member, and
wherein the first area, the second area, and the third area overlap one another such that any two of the first mask, the second mask, or the third mask cannot be simultaneously mounted to the upper surface of the planar member.

20. The body part positioning structure of claim 1, wherein the first mask and the second mask comprise differently configured mask structures, with each of the mask structures having a material that form fits to the at least a portion of the body part to secure the at least a portion of the body part upon the upper surface of the planar member.

\* \* \* \* \*